United States Patent
Tanaka

(10) Patent No.: US 6,773,161 B2
(45) Date of Patent: Aug. 10, 2004

(54) X-RAY DIAGNOSTIC APPARATUS

(75) Inventor: Hideaki Tanaka, Otawara (JP)

(73) Assignee: Kabushiki Kaisha Toshiba, Tokyo (JP)

(*) Notice: Subject to any disclaimer, the term of this patent is extended or adjusted under 35 U.S.C. 154(b) by 0 days.

(21) Appl. No.: 10/202,860

(22) Filed: Jul. 26, 2002

(65) Prior Publication Data

US 2003/0021386 A1 Jan. 30, 2003

(30) Foreign Application Priority Data

Jul. 27, 2001 (JP) ........................................ 2001-228195

(51) Int. Cl.⁷ ............................................... H05G 1/02
(52) U.S. Cl. ...................... 378/198; 378/196; 378/177; 378/179
(58) Field of Search ................ 378/195–198, 378/177, 179, 25–27

(56) References Cited

U.S. PATENT DOCUMENTS 3,818,516 A * 6/1974 Hopper et al. ................. 5/611
5,768,336 A * 6/1998 Khutoryansky et al. ..... 378/116
5,829,076 A * 11/1998 Csikos et al. .................. 5/601
6,382,832 B1 * 5/2002 Schwieker et al. .......... 378/196

FOREIGN PATENT DOCUMENTS

JP        11-206744         8/1999

OTHER PUBLICATIONS

Phillips Medical Systems, Philips Duo Diagnost, (http://www.medical.philips.com), 5 pages.

* cited by examiner

Primary Examiner—Craig E. Church
Assistant Examiner—Jurie Yun
(74) Attorney, Agent, or Firm—Oblon, Spivak, McClelland, Maier & Neustadt, P.C.

(57) ABSTRACT

An X-ray diagnostic apparatus includes an arm supporting an X-ray tube and an X-ray detector, and a tilting bed. A joining mechanism detachably joins the arm to the bed. An arm support mechanism freely supports the arm. While the arm is joined to the bed, the arm follows a tilting of the bed.

2 Claims, 8 Drawing Sheets

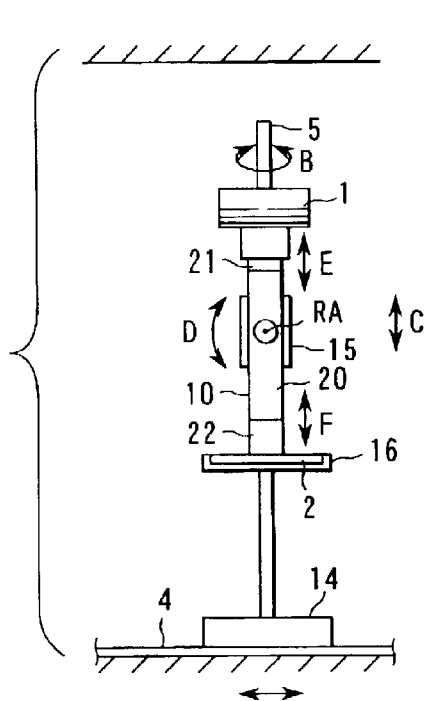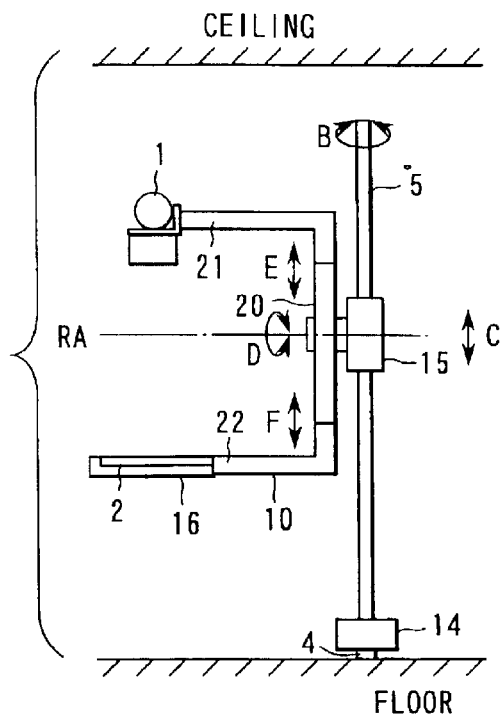
FIG. 3A   FIG. 3B
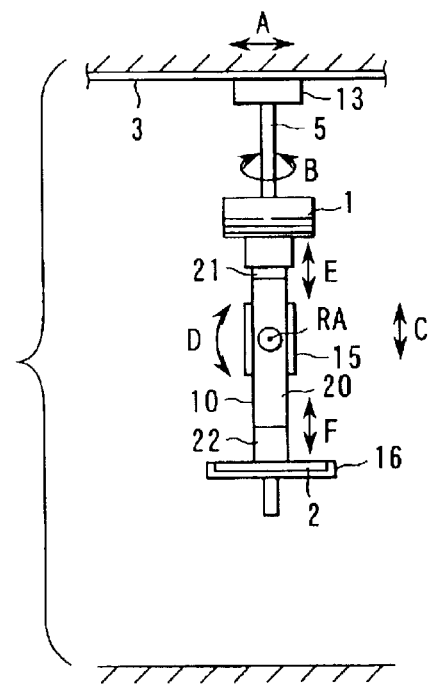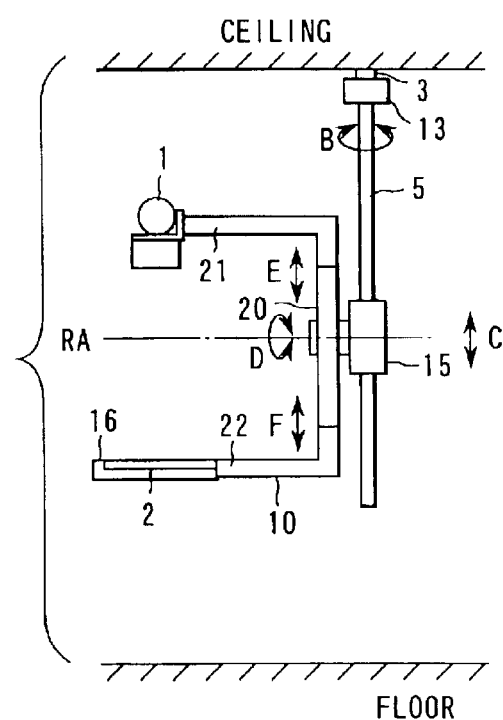
FIG. 4A   FIG. 4B

X-RAY DIAGNOSTIC APPARATUS

CROSS-REFERENCE TO RELATED APPLICATIONS

This application is based upon and claims the benefit of priority from the prior Japanese Patent Application No. 2001-228195, filed Jul. 27, 2001, the entire contents of which are incorporated herein by reference.

BACKGROUND OF THE INVENTION

1. Field of the Invention

The present invention relates to an X-ray diagnostic apparatus having a tilting bed.

2. Description of the Related Art

X-ray diagnostic apparatuses, many of X-ray diagnostic apparatuses designed for the digestive system such as the stomach, duodenum, and small intestine as targets to be imaged, in particular, are equipped with a bed which can freely tilt in the range of a vertical position (+30°) to the head down vertical position (−30°). This makes it possible to hold an object to be examined in a posture in which an optimal effect of a contrast medium can be obtained.

A cassette or X-ray detector is mounted below the top of the bed. An X-ray tube is supported by a support at a high position where it faces the X-ray detector. The support is fixed to the frame of the bed. With this structure, the support is tilted together with the bed.

Such a digestive system X-ray diagnostic apparatus has the following problem to be solved.

As is known, an X-ray tube constitutes an X-ray diagnostic apparatus, together with a stop unit and the like. The X-ray diagnostic apparatus is very heavy. A support which supports the heavy X-ray diagnostic apparatus, a bed frame which supports the X-ray diagnostic apparatus together with the support, and a base which supports the bed frame are required to have high rigidity. In addition, very large driving force is required to quickly and smoothly tilt the heavy X-ray diagnostic apparatus, heavy support, and heavy bed frame.

Such a heavy, large X-ray diagnostic apparatus narrows the space where a doctor makes an approach to a patient during IVR (interventional radiology) in which treatment is done under fluoroscopy.

The invention disclosed in Jpn. Pat. Appln. KOKAI Publication No. 11-206744 has a structure in which a C-arm which supports an X-ray tube unit together with an image intensifier and TV camera is cantilevered by a stand different from a bed, and is especially characterized by a design in which the tilt axis of the arm stand is matched with the tilt axis of the bed. This design allows the shared use of a drive source for bed tilting and C-arm tilting.

This design, however, leads to an increase in the size of the arm stand, and requires the arm stand to be located close to the bed. This limits the approach space to a narrow space. In addition, according to the above design, the arm stand and the bed are always set in pair. For this reason, an object to be examined on a member other than the top, e.g., a stretcher, cannot be imaged.

BRIEF SUMMARY OF THE INVENTION

It is an object of the present invention to increase the approach space and the degree of freedom in imaging in an X-ray diagnostic apparatus having a tilting bed.

According to the first aspect of the present invention, there is provided an X-ray diagnostic apparatus comprising an arm supporting an X-ray tube and an X-ray detector, a tilting bed, a joining mechanism detachably joining the arm to the bed, and an arm support mechanism freely supporting the arm such the arm follows a tilting of the bed According to the second aspect of the present invention, there is provided an X-ray diagnostic apparatus comprising a tilting bed, an arm supporting an X-ray tube and an X-ray detector and being structurally isolated from the bed, and an arm support mechanism being structurally isolated from the bed and freely supporting the arm.

According to the third aspect of the present invention, there is provided an X-ray diagnostic apparatus comprising a tilting bed, an arm mounting an X-ray tube and an X-ray detector, an arm support mechanism configured to freely support the arm, a rotation driving unit configured to drive rotation of the arm, a horizontal displacement driving unit configured to drive horizontal displacement of the arm, a rise/fall driving unit configured to drive rising/falling of the arm, and a control unit configured to control the rotation driving unit, the horizontal displacement driving unit, and the rise/fall driving unit to make the arm rotate, translate, and rise/fall in accordance with tilting of the bed.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 3A is a front view showing another example of the structure of the arm support mechanism in FIG. 1;

FIG. 3B is a front view showing still another example of the structure of the arm support mechanism in FIG. 1;

FIG. 4A is a front view showing still another example of the structure of the arm support mechanism in FIG. 1;

FIG. 4B is a front view showing still another example of the structure of the arm support mechanism in FIG. 1;

DETAILED DESCRIPTION OF THE INVENTION

An X-ray diagnostic apparatus according to an embodiment of the present invention will be described below with reference to the views of the accompanying drawing.

Figure 1:
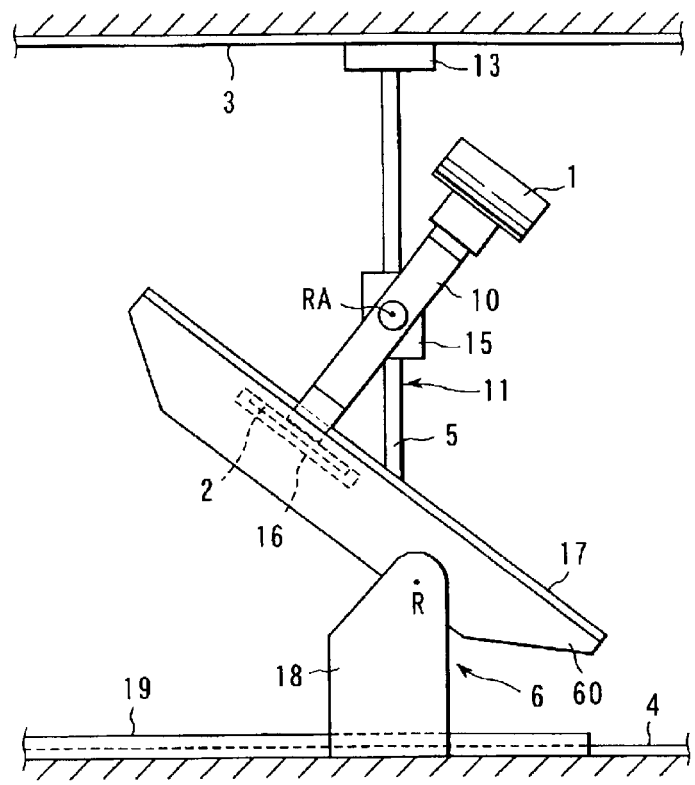
FIG. 1 is a side view of an X-ray diagnostic apparatus according to an embodiment of the present invention.
Figure 2A:
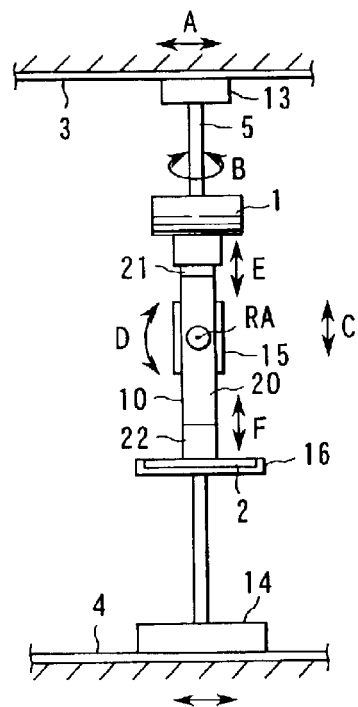
FIG. 2A is a front view of an arm support mechanism in FIG. 1.
Figure 2B:
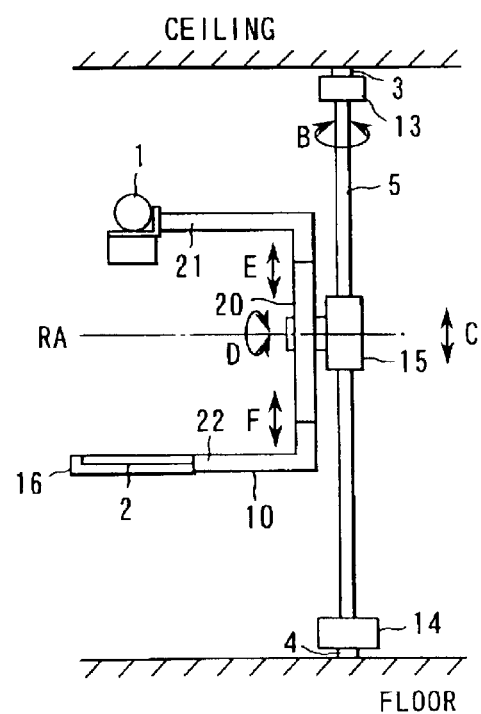
FIG. 2B is a side view of the arm support mechanism in FIG. 1.

FIG. 1 is a side view of the X-ray diagnostic apparatus according to this embodiment. FIGS. 2A and 2B are front and side views of an arm support mechanism in FIG. 1. A bed 6 has a bed body 60 which supports a top 17 and a tilt stand 18 which supports the bed body 60 so as to allow it to tilt. The tilt stand 18 is movably mounted on a rail 19. Reference symbol R denotes a rotational axis for tilting. The longitudinal direction of the top 17 is parallel to the rail 19. The rotational axis R for tilting is perpendicular to the longitudinal direction of the top 17.

An arm 10 has a U- or C-shape. An X-ray tube 1 is mounted on one end of the arm 10. An X-ray detector 2 is mounted on the other end of the arm 10. The X-ray detector 2 opposes the X-ray tube 1. As the X-ray detector 2, a flat panel detector (PDP) is used. The flat panel detector has a plurality of detection elements arrayed in the form of a matrix. Each detection element is formed from a combination of a scintillator element and a photodiode element or a semiconductor element for directly converting X-rays into charges.

An arm support mechanism 11 freely supports the arm 10. The arm 10 and arm support mechanism 11 are physically separated from the bed 6. The arm support mechanism 11 has a vertical support 5. The vertical support 5 is provided to freely move in the horizontal direction (arrow A). Horizontal displacement bases 13 and 14 are provided a ceiling rail 3 and floor rail 4 respectively. The ceiling rail 3 and floor rail 4 are parallel to the longitudinal direction of the top 17. The horizontal displacement bases 13 and 14 support the vertical support 5 to allow it to freely rotate about the axis (arrow B).

The present invention is not limited to the vertical support 5 that is supported on both the ceiling and the floor. As shown in FIGS. 3A and 3B, the vertical support 5 may be cantilevered from the floor. Alternatively, as shown in FIGS. 4A and 4B, the vertical support 5 may be cantilevered and suspended from the ceiling.

An arm holder 15 is supported on the vertical support 5 to freely rise/fall along the axial direction of the vertical support 5 (arrow C). The arm holder 15 supports the arm 10 to allow it to tilt (arrow D). A rotational axis RA of the arm 10 is parallel to the rotational axis R for tilting of the bed 6.

The arm 10 has a vertical arm 20 supported on the arm holder 15 to freely rotate about the axis. The vertical arm 20 has a cylindrical shape. A horizontal arm 21 is extendably inserted into one opening of the vertical arm 20 (arrow E). The X-ray tube 1 is fixed on the horizontal arm 21. A horizontal arm 22 is extendably inserted into the other opening of the vertical arm 20 (arrow F). A detector frame 16 that detachably holds the X-ray detector 2 is fixed on the horizontal arm 22. The X-ray detector 2 can be removed from the detector frame 16, and a film cassette can be mounted on the frame instead. At least one of the X-ray detector 2 and the film cassette may require an adaptor to be mounted on the detector frame 16.

By inserting the horizontal arm 21 into the vertical arm 20 deeply or inserting the horizontal arm 22 into the vertical arm 20 deeply, the distance (SID) between the X-ray tube 1 and the X-ray detector 2 can be decreased. In contrast to this, the distance (SID) between the X-ray tube 1 and the X-ray detector 2 can be increased by inserting the horizontal arm 21 into the vertical arm 20 shallowly or inserting the horizontal arm 22 into the vertical arm 20 shallowly.

In order to make the arm 10 balance on the rotational axis RA, the distance from the rotational axis RA to the X-ray tube 1 and the distance from the rotational axis RA to the X-ray detector 2 are designed in accordance with the respective weights. In order to keep the arm 10 in balance, the vertical arm 20 incorporates a link mechanism required to make one of the horizontal arms 21 and 22 extend/contract in synchronism with the extending/contracting movement of the other horizontal arm. A structure having no counterweight mounted to keep the arm 10 in balance realizes a reduction in the weight of the arm 10. A reduction in the weight of the arm 10 realizes light, smooth tilting of the arm 10.

The vertical support 5 has a cylindrical shape. The vertical support 5 incorporates a power assist mechanism or weight balance mechanism for allowing the arm holder 15 to lightly rise and fall. In order to realize light, smooth movement, the horizontal displacement bases 13 and 14 are coupled to the power assist mechanism (not shown).

The above structure of the arm support mechanism 11 allows the arm 10 to lightly move within the vertical plane defined by the rails 3 and 4 and to lightly tilt at each position. Rotation of the vertical support 5 about the axis realizes swinging of the arm 10. This makes it possible to place the arm 10 at an angle of 90° or 180° with respect to the bed 6. At this angle, a patient on the stretcher can be imaged. In addition, this angle allows an omnidirectional approach to the patient on the top 17.

The arm 10 freely supported by the arm support mechanism 11 is detachable from the bed 6. While the arm 10 is joined to the bed 6, free movement of the arm 10 allows it to tilt, translate, and rise/fall upon tilting of the bed 6.

Figure 5A:
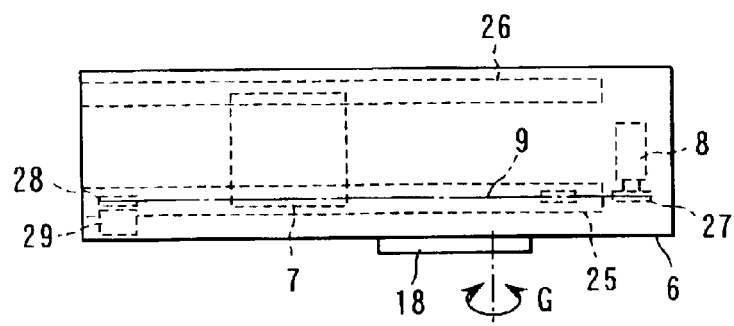
FIG. 5A is a plan view of a tilting bed in FIG. 1.
Figure 5B:
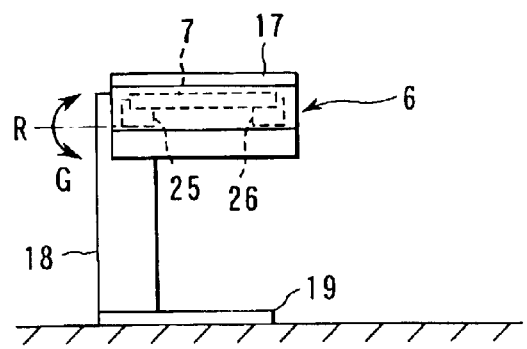
FIG. 5B is a front view of the tilting bed in FIG. 1.
Figure 5C:
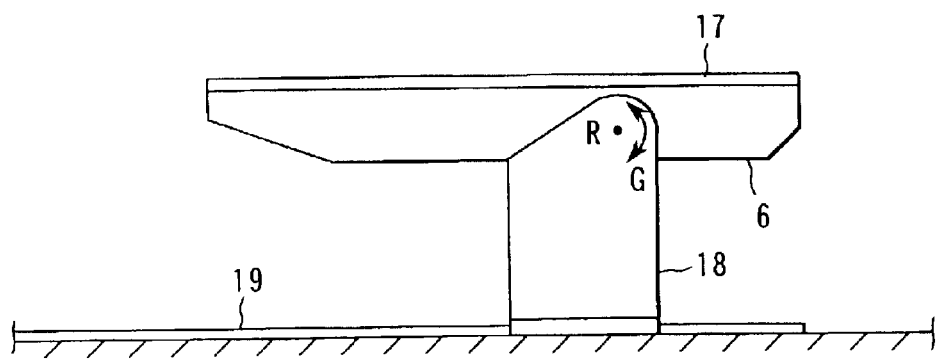
FIG. 5C is a side view of the tilting bed in FIG. 1.

Reference numeral 7 in FIGS. 5A, 5B, and 5C denotes a joining frame for joining the arm 10 to the bed 6. The joining frame 7 is placed below the top 17. The bed body 60 has a firm frame. Two parallel joining frame rails 25 and 26 are mounted on this frame so as to be parallel to the longitudinal direction. The joining frame 7 is movably provided on the joining frame rails 25 and 26. A chain 9 is looped around sprockets 27 and 28 so as to be parallel to the joining frame rails 25 and 26. The sprocket 27 is connected to the drive shaft of a drive source (servo motor) 8. The joining frame 7 is fixed to a specific portion of the chain 9. When the drive source 8 rotates, the chain 9 circulates. In accordance with the circulation of the chain 9, the joining frame 7 moves along the joining frame rails 25 and 26. In order to fix the joining frame 7 at an arbitrary position, the sprocket 28 has an electromagnetic brake 29. The electromagnetic brake 29 is released while the X-ray detector 2 is positioned to a region to be imaged. The electromagnetic brake 29 fixes the joining frame 7 during a joining period and imaging period.

Figure 6A:
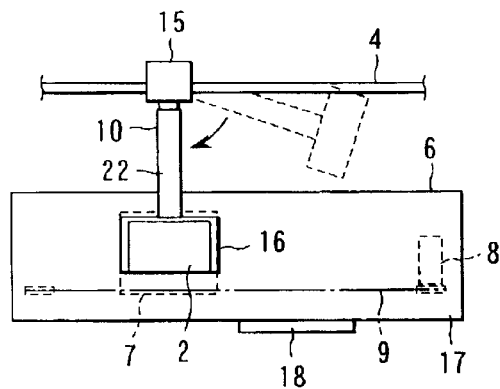
FIG. 6A is a plan view showing how a C-arm is joined to the bed in FIG. 1.
Figures 6B, 6C:
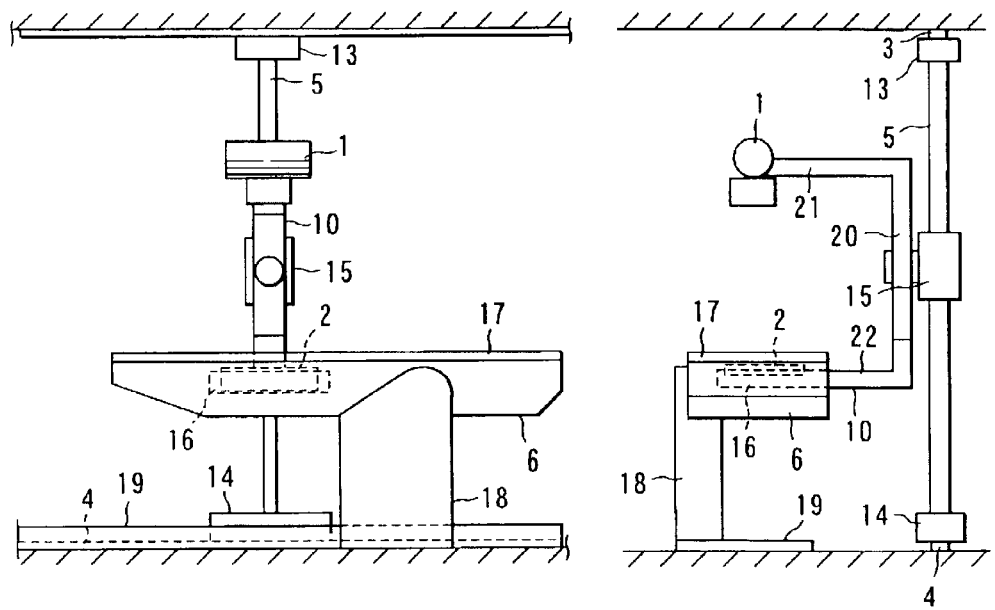
FIG. 6B is a side view showing how the C-arm is joined to the bed in FIG. 1.
FIG. 6C is a front view showing how the C-arm is joined to the bed in FIG. 1.

As shown in FIGS. 6A, 6B, and 6C, the bed body 60 is set in a horizontal position to join the detector frame 16 to the joining frame 7. The joining frame 7 is locked at a position on the swinging path of the detector frame 16. The detector frame 16 can be easily joined to the joining frame 7 by swinging the arm 10. The detector frame 16 is removed from the joining frame 7 in the same manner. The detector frame 16 is fixed to the joining frame 7 with screws, a plunger, or an electromagnetic brake.

Figure 7A:
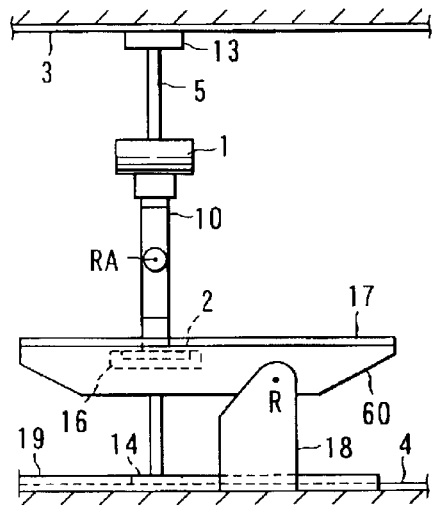
FIGS. 7A to 7E are side views showing how the C-arm follows the tiling movement of the bed in this embodiment.
Figure 7B:
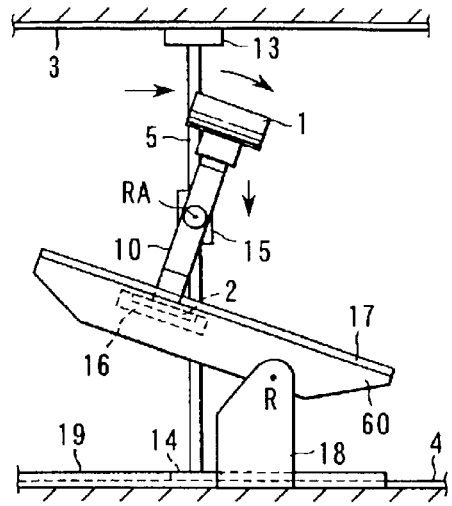
Figure 7C:
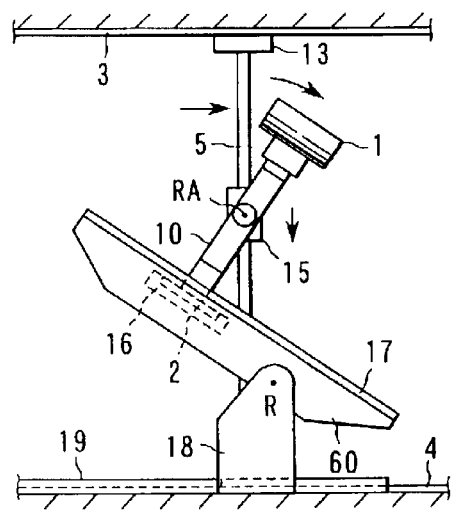
Figure 7D:
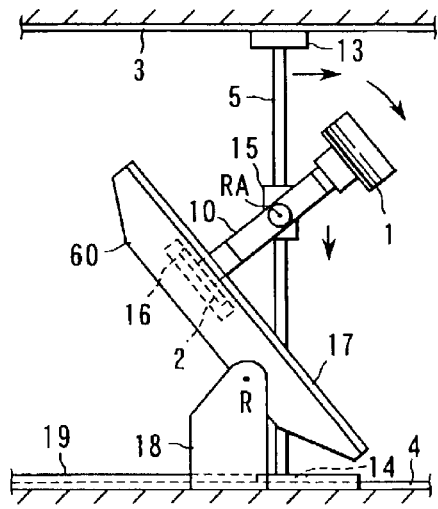
Figure 7E:
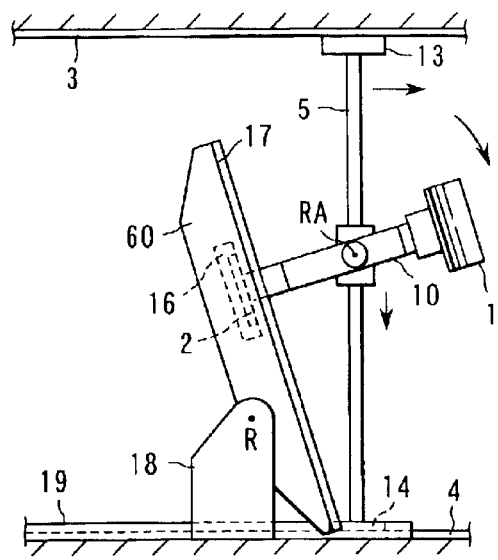

Actual imaging operation will be described below. First of all, as shown in FIG. 7A, in a preparatory stage, the bed body 60 is positioned horizontal, and the joining frame 7 is locked by the electromagnetic brake 29. The arm 10 is swung to insert and fix the detector frame 16 in the joining frame 7. The joining frame 7 is then released. The arm 10 is translated, together with the joining frame 7, to position the X-ray detector 2 to a region to be imaged. After positioning, the joining frame 7 is locked by the electromagnetic brake 29. The horizontal arms 21 and 22 are arbitrarily extended/contracted with respect to the vertical arm 20 to adjust the SID.

As shown in FIGS. 7A to 7E, the bed body 60 is gradually raised from the horizontal position. This movement is done by a bed drive source with electromotive force. On the other hand, tilting, rising/falling, and horizontal displacement of the arm 10 are in free states, and hence a combination of the three types of movements, i.e., tilting, rising/falling, and horizontal displacement, makes the arm 10 gradually tilt upon tilting of the bed body 60.

The movement of the arm 10 that follows the tilting movement of the bed body 60 can be easily understood by giving attention to the movement of the tilt rotational axis RA. Upon the tilt rotation of the bed body 60, the tilt rotational axis RA moves on the arc which is centered on the tilt rotational axis R of the bed body 60 and has a radius equal to the distance between the tilt rotational axis RA and the tilt rotational axis R in the initial state upon completion of joining. The tilt angle of the arm 10 changes upon the movement of the tilt rotational axis RA in the form of an arc while the crossing angle defined by the central axis of the arm 10 and a tangent on the arc traced by the tilt rotational axis RA in the initial state upon completion of joining is kept unchanged. That is, the arm 10 rotates from the vertical position through the same angle as the tilt angle of the bed 6.

Such tilting, rising/falling, and horizontal displacement of the arm 10 can be satisfactorily realized by the force generated by only the drive source for bed tilting owing to light, the smooth movement of the arm 10 which is realized by the arm support mechanism 11 as described above. Therefore, for tilting, rising/falling, and horizontal displacement of the arm 10, no special drive source other than the drive source for bed tilting is required.

As described above, according to this embodiment, installing the arm support mechanism 11 separately from the bed 6 leads to a reduction in the size of the tilt stand 18 for the bed 6. In addition, the tilt drive source can be formed from a motor with a relatively low torque. Furthermore, since the light movement of the arm 10 is realized by the arm support mechanism 11, the arm 10 can be made to follow tilting of the bed body 60 without stress. This eliminates the necessity of a special drive source for tilting, rising/falling, and horizontal displacement of the arm 10 other than the drive source for bed tilting and makes it possible to simplify the driving system. Since the arm support mechanism 11 is provided independently of the bed 6, and the X-ray tube 1 and X-ray detector 2 are supported by the arm 10, the approach space to the patient on the top 17 can be expanded.

In addition, rotation of the vertical support 5 about the axis makes the arm 10 be set in a direction different from that of the bed 6 so as to allow the patient on, for example, a stretcher other than the bed 6 to be imaged. Alternatively, the arm 10 is completely retreated from the bed 6 to allow a full approach to the patient on the top 17.

As described above, the movable portion of the arm 10 is associated with tilt rotation, rising/falling, horizontal displacement, swinging, and extension/contraction for a change in SID, and horizontal displacement of the joining frame 7 of the bed 6. For these movements, for example, this apparatus is equipped with electromagnetic brakes as lock/release (free) switching means. It is very cumbersome to manually lock/release these electromagnetic brakes separately. In addition, the combination of electromagnetic brakes to be locked must be changed between a preparatory stage for initial settings for swinging of the arm 10, SID adjustment, imaging position setting (joining frame movement), and the like and an imaging stage, and an operation error may occur. In this embodiment, therefore, operation of the electromagnetic brakes is automated by electronic control, thereby realizing high operability.

Figure 8:
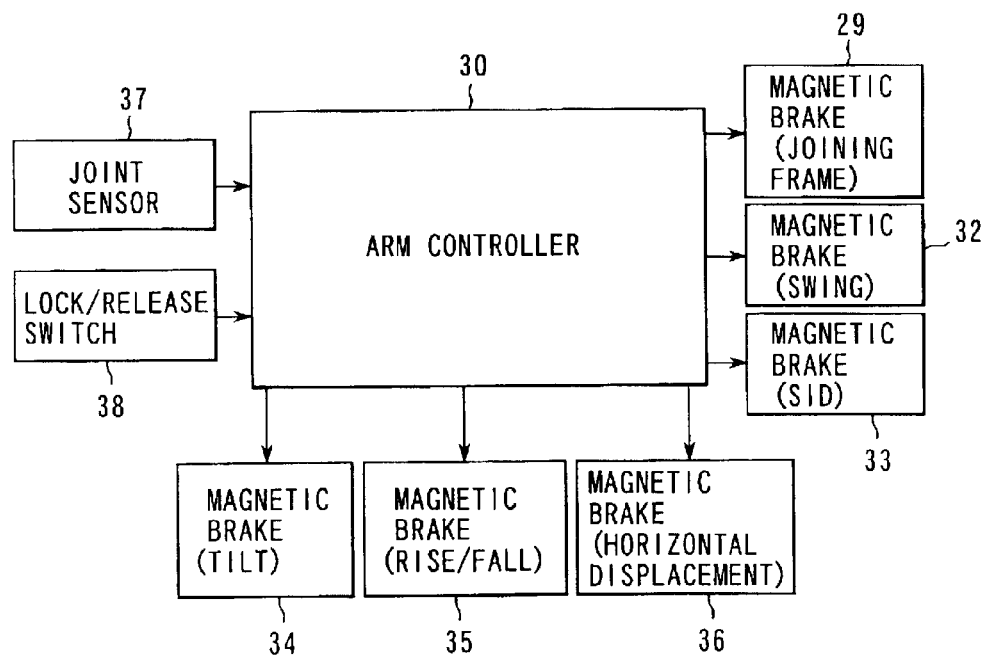
FIG. 8 is a view showing an electromagnetic brake system for the movable portion of the C-arm in this embodiment.

FIG. 8 shows a control system for the electromagnetic brakes for the movable portion of the arm 10. An arm controller 30 controls the operation (locking/releasing) of electromagnetic brake 29 and electromagnetic brakes 32, 34, 35, and 36. The electromagnetic brake 29 corresponds to the movement of the joining frame 7. The electromagnetic brake 32 corresponds to swinging of the arm 10. The electromagnetic brake 33 corresponds to the SID (extension/contraction of the horizontal arms 21 and 22). The electromagnetic brake 34 corresponds to tilt rotation of the arm 10. The electromagnetic brake 35 corresponds to rising/falling (rising/falling of the arm holder 15) of the arm 10. The electromagnetic brake 36 corresponds to horizontal displacement (horizontal displacement of the vertical support 5) of the arm 10.

The arm controller 30 changes control on the electromagnetic brakes 29, 32, 34, 35, and 36 between an imaging preparation period, an period after imaging, and an imaging period. In an imaging preparation period, setting operation from the retreat position to the imaging position (swinging of the arm 10), SID adjustment, positioning operation for the imaging position, joining of the detector frame 16 to the joining frame 7 (joining of the arm 10 to the bed 6) are performed. After imaging, removal of the detector frame 16 from the joining frame 7 and retreating operation from the imaging position to the retreating position (swinging of the arm 10) are performed.

The arm controller 30 identifies an imaging preparation period, an period after imaging, and an imaging period on the basis of outputs from a joint sensor 37 and lock/release switch 38. The joint sensor 37 is set on a necessary structure at a necessary position to detect that the detector frame 16 is mounted on the joining frame 7, and the detector frame 16 is fixed to the joining frame 7 with setting screws or the like. While the detector frame 16 is fixed to the joining frame 7, the joint sensor 37 is kept ON. While the detector frame 16 is not fixed to the joining frame 7, the joint sensor 37 is kept OFF.

The lock/release switch 38 is an operating portion which is operated by an operator to send an instruction to lock or release the electromagnetic brakes 29, 32, 34, 35, and 36 to the apparatus. The lock/release switch 38 is placed at a position where the operator can operate with his/her hand, e.g., a position on a side surface of the bed 6. When the operator wants to lock the electromagnetic brakes 29, 32, 34, 35, and 36, he/she turns on the lock/release switch 38. When the operator release the locked states, he/she turns off the lock/release switch 38.

The ON and OFF states of the joint sensor 37 and the ON and OFF states of the lock/release switch 38 make four combinations. When the lock/release switch 38 is OFF and the joint sensor 37 is ON, the arm controller 30 determines that the current state corresponds to an imaging period. With other combinations, the arm controller 30 determines an imaging preparation period or an period after imaging.

In an imaging preparation period or after imaging, the arm controller 30 controls the states of the electromagnetic brakes 29, 32, 34, 35, and 36 in accordance with the ON/OFF state of the lock/release switch 38. When the lock/release switch 38 is ON, the arm controller 30 operates all the electromagnetic brakes 29, 32, 34, 35, and 36 to set the arm 10 in the locked state. This inhibits all the movements of the arm 10. When the lock/release switch 38 is OFF, the arm controller 30 operates all the electromagnetic brakes 29, 32, 34, 35, and 36 to set the arm 10 in the released state. This permits all the movements of the arm 10. In an imaging preparation period or after imaging, therefore, the operator can easily adjust the SID and position an imaging position by freely moving the arm 10.

After the SID and imaging position are determined, the joining frame 7 is mounted on the detector frame 16, and the detector frame 16 is fixed to the joining frame 7 with set screws or the like. Upon this operation, the joint sensor 37 is switched from the OFF state to the ON state. This makes the arm controller 30 recognize that imaging is being done. The arm controller 30 then switches the electromagnetic brake 32 for swinging and the electromagnetic brake 33 for SID from the released state to the locked state, thus inhibiting changes in the swinging of the arm 10 and SID. This makes it possible to produce a state equivalent to the state wherein the arm 10 and bed 6 are structurally joined to each other.

The arm controller 30 maintains the electromagnetic brake 34 for tilt rotation, the electromagnetic brake 35 for erasing/falling, and the electromagnetic brake 36 for horizontal displacement in the released state.

As described above, during an imaging period, the movement of the arm 10 is inhibited concerning the movement of the joining frame 7 and swinging and SID is inhibited, whereas the movement of the arm 10 is permitted concerning tilt rotation, rising/falling, and horizontal displacement. This therefore makes it possible to optimize the environment to cause the arm 10 to follow the tilting movement of the bed 6 while maintaining the positions and angles of the X-ray tube 1 and X-ray detector 2 relative to the top 17.

When it becomes necessary to retreat the arm 10 from the bed 6 for some reason during imaging or after imaging, the joining frame 7 is removed from the detector frame 16. Upon this operation, the joint sensor 37 is switched from the ON state to the OFF state. As a consequence, the arm controller 30 recognizes a shift from the imaging period to a period after imaging, and returns the electromagnetic brake 32 for swinging and the electromagnetic brake 33 for SID from the locked state to the released state, thereby permitting the arm 10 to freely swing and move for SID adjustment. On the other hand, the arm controller 30 maintains the electromagnetic brake 34 for tilt rotation, the electromagnetic brake 35 for rising/falling, and the electromagnetic brake 36 for horizontal displacement released. This makes all the movements of the arm 10 free. Therefore, the operator can freely move the arm 10 and retreat it as needed.

As described above, even if the lock/release switch 38 is OFF, when the joint sensor 37 is ON, the electromagnetic brake 34 for tilt rotation, the electromagnetic brake 35 for rising/falling, and the electromagnetic brake 36 for horizontal displacement are released. However, the electromagnetic brake 32 for swinging and the electromagnetic brake 33 for SID are locked. This makes it possible to automatically set the environment to make the arm 10 follow the tilting movement of the bed 6 while maintaining the positions and angles of the arm 10, X-ray tube 1, and X-ray detector 2 relative to the top 17. That is, there is no need to perform cumbersome work of separately operating the electromagnetic brakes such that the electromagnetic brakes are set in the locked state, and the electromagnetic brakes 35 and 36 are released, in order to set this environment.

According to the above description, while the arm 10 is joined to the bed body 60, tilt rotation, rising/falling, and horizontal displacement of the arm 10 are permitted to make the arm 10 follow the tilting movement of the bed body 60. However, tilt rotation, rising/falling, and horizontal displacement of the arm 10 may be done with electromotive force to follow the tilting movement of the bed body 60 without joining the arm 10 to the bed body 60.

Figure 9:
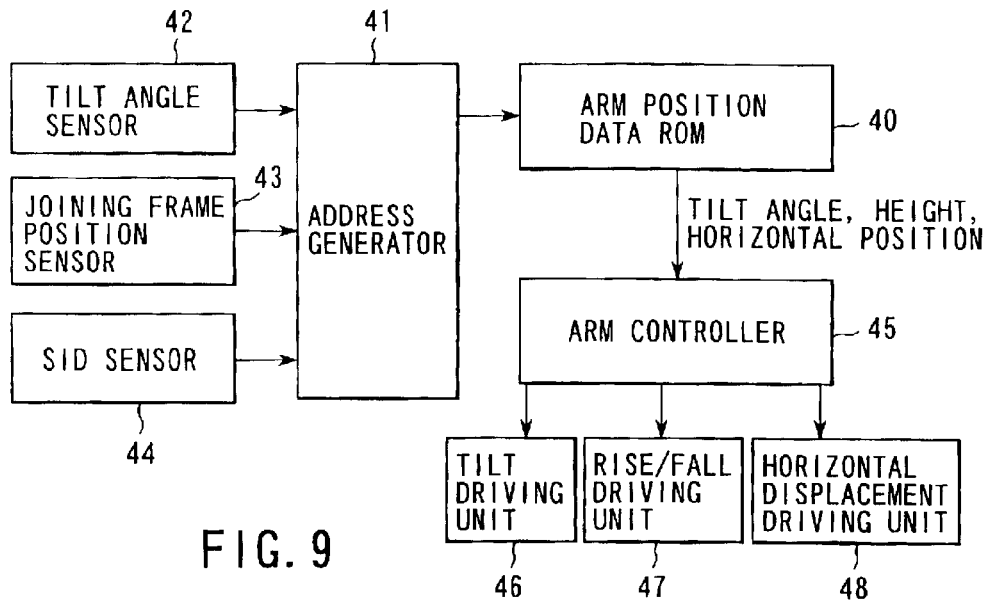
FIG. 9 is a block diagram showing a control system for making the C-arm follow the tilting movement of the bed in a modification to this embodiment.

FIG. 9 shows a follow-up control system. In order to make the arm 10 follow the tilting movement of the bed body 60, SID (the distance between the X-ray tube 1 and the X-ray detector 2) information is required as well as the tilt angle of the bed body 60. These pieces of information are detected by a tilt angle sensor 42, joining frame position sensor 43, and SID sensor 44. Outputs from these sensors 42, 43, and 44 are sent to the address generator 41. The address generator 41 supplies address signals corresponding to the tilt angle of the bed 6, the position of the joining frame 7, and the SID to a follow-up data ROM 40. The tilt rotational angle, height, and horizontal displacement position of the arm 10 are calculated in advance with respect to each of a plurality of combinations of the tilt angles of the bed 6, the positions of the joining frame 7, and SID, and are respectively stored as data at the corresponding addresses in the arm position data ROM 40.

As described above, the movement and rotational movement of the arm 10 can be easily understood by giving attention to the tilt rotational axis RA. The tilt rotational axis RA moves on the arc which is centered on the tilt rotational axis R of the bed body 60 and has a radius equal to the distance between the tilt rotational axis RA and the tilt rotational axis R in the initial state upon completion of joining. The tilt angle of the arm 10 changes upon the movement of the tilt rotational axis RA in the form of an arc while the crossing angle defined by the central axis of the arm 10 and a tangent on the arc traced by the tilt rotational axis RA in the initial state upon completion of joining is kept unchanged. That is, the arm 10 rotates from the vertical position through the same angle as the tilt angle of the bed 6. By calculating the tilt rotational angle, height, and horizontal displacement position of the arm 10 at each position on the arc path along which the rotational axis RA moves in this manner, data required to follow the tilting movement of the bed 6 can be obtained.

A controller 45 therefore controls a tilt driving unit 46, rise/fall driving unit 47, and horizontal displacement driving unit 48 to make the arm 10 tilt/rotate, rise/fall, and horizontally displace in accordance with the data of the tilt rotational angle, height, and horizontal displacement position of the arm 10 which are read out in accordance with outputs from the tilt angle sensor 42, joining frame position sensor 43, and SID sensor 44, thereby driving tilt rotation, rising/falling, and horizontal displacement of the arm 10 with electromotive force so as to follow the tilting movement of the bed 6.

Figure 10:
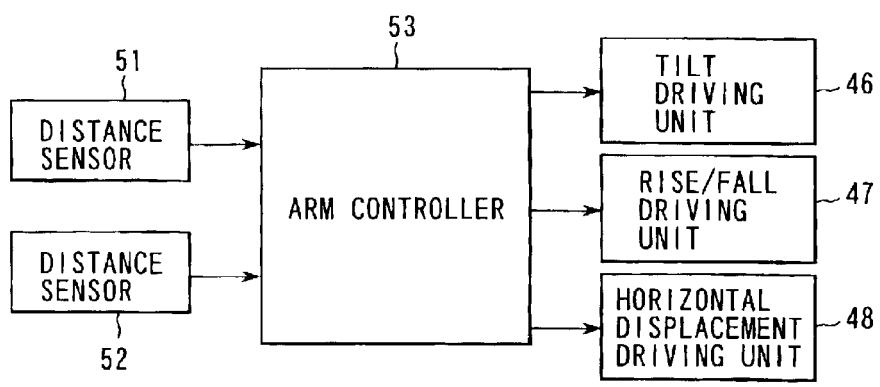
FIG. 10 is a block diagram showing a control system for making the C-arm follow the tilting movement of the bed in another modification to this embodiment.
Figure 11:
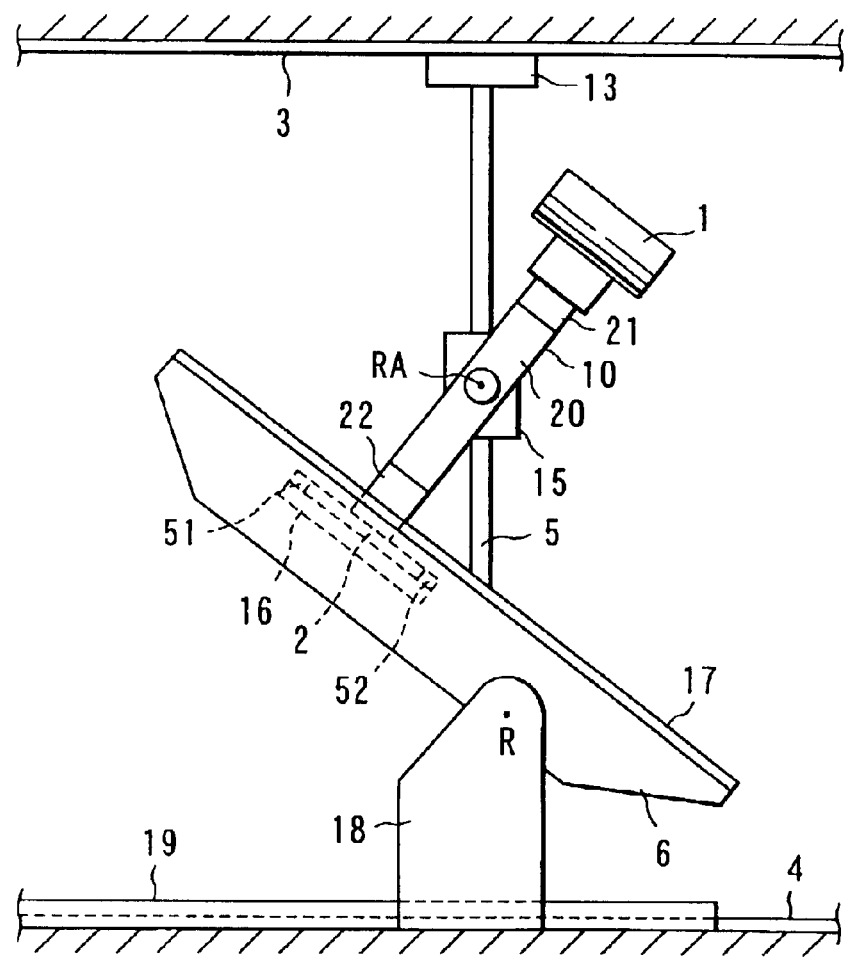
FIG. 11 is a side view showing the mount positions of distance sensors in FIG. 10.

Note that this control system can be simplified. For example, as shown in FIGS. 10 and 11, distance sensors 51 and 52 for measuring the distance between the top 17 and the X-ray detector 2 are attached to at least two portions, i.e., front and rear portions of the X-ray detector 2, and a controller 53 may control the driving units 46, 47, and 48 so as to keep the distances between the top 17 and the front and rear portions of the X-ray detector 2 at predetermined distances on the basis of outputs from the distance sensors 51 and 52.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray diagnostic apparatus comprising:

an arm supporting an X-ray tube and an X-ray detector;

a tilting bed;

a joining mechanism configured to detachably join the arm to the bed;

an arm support mechanism configured to freely support the arm such that the arm follows a tilting of the bed;

wherein the arm includes a detector frame on which the X-ray detector is to detachably be mounted; and wherein the joining mechanism includes a joining frame which is joined to the detector frame, a mechanism of supporting the joining frame to allow the joining frame to freely move in a longitudinal direction of the bed, and a mechanism of locking the joining frame at an arbitrary position.

2. An X-ray diagnostic apparatus comprising:

an arm supporting an X-ray tube and an X-ray detector;

a tilting bed;

a joining mechanism configured to detachably join the arm to the bed;

an arm support mechanism configured to freely support the arm such that the arm follows a tilting of the bed;

wherein the arm support mechanism includes electromagnetic brakes corresponding to rotation, horizontal displacement, and rising/falling of the arm; and further comprising a sensor which detects joining of the arm to the bed, and a control unit which releases the electromagnetic brake when the sensor detects that the arm is joined to the bed.

* * * * *